(12) United States Patent
Filkins et al.

(10) Patent No.: US 8,532,398 B2
(45) Date of Patent: Sep. 10, 2013

(54) METHODS AND APPARATUS FOR OPTICAL SEGMENTATION OF BIOLOGICAL SAMPLES

(75) Inventors: Robert John Filkins, Niskayuna, NY (US); Bahman Ebrahimi Kashef, Latham, NY (US); Krenar Tasimi, Naugatuck, CT (US)

(73) Assignee: General Electric Company, Niskayuna, NY (US)

( * ) Notice: Subject to any disclaimer, the term of this patent is extended or adjusted under 35 U.S.C. 154(b) by 771 days.

(21) Appl. No.: 12/732,272

(22) Filed: Mar. 26, 2010

(65) Prior Publication Data
US 2011/0235875 A1 Sep. 29, 2011

(51) Int. Cl.
*G06K 9/76* (2006.01)
*G06K 9/00* (2006.01)

(52) U.S. Cl.
USPC .......................................... 382/211; 382/128

(58) Field of Classification Search
USPC ............................ 356/39; 382/133, 134, 211
See application file for complete search history.

(56) References Cited

U.S. PATENT DOCUMENTS

| | | | |
|---|---|---|---|
| 5,587,832 A | 12/1996 | Krause | |
| 7,005,654 B2* | 2/2006 | Seyfried | 250/458.1 |
| 7,015,444 B2* | 3/2006 | Kawano et al. | 250/201.3 |
| 7,034,983 B2* | 4/2006 | DeSimone et al. | 359/290 |
| 7,346,776 B2* | 3/2008 | Levy et al. | 713/176 |
| 7,352,504 B2* | 4/2008 | Hirooka et al. | 359/327 |
| 7,355,716 B2* | 4/2008 | de Boer et al. | 356/479 |
| 7,532,323 B2* | 5/2009 | Tang et al. | 356/317 |
| 2002/0145610 A1* | 10/2002 | Barilovits et al. | 345/538 |

FOREIGN PATENT DOCUMENTS

| | | |
|---|---|---|
| WO | 02075292 A2 | 9/2002 |
| WO | 2007062039 A2 | 5/2007 |

* cited by examiner

*Primary Examiner* — Sind Phongsvirajati
*Assistant Examiner* — John Go
(74) *Attorney, Agent, or Firm* — Eileen B. Gallagher

(57) ABSTRACT

A method for the imaging of protein expression and location in biological samples using optical segmentation is provided. The steps comprise acquiring a fluorescent image of a biological sample, analyzing the image and generating a masking pattern corresponding to a specific structure within the biological sample, transforming the masking pattern into the spatial coordinates of a digital micro-mirror device (DMD) which may then be projected onto the biological sample and obtaining a masked fluorescent image. Also provided is an image analysis system for imaging of protein expression and location in biological samples using optical segmentation.

17 Claims, 6 Drawing Sheets

C          D

METHODS AND APPARATUS FOR OPTICAL SEGMENTATION OF BIOLOGICAL SAMPLES

BACKGROUND

In a typical fluorescent imaging scenario for molecular pathology, dyes are used to label specific proteins or subcellular compartments. Often the proteins of greatest interest are expressed at low levels, and in the course of exciting the fluorescent reporters for imaging; the entire biological sample such as a tissue section is illuminated, generating fluorescence emission due to endogenous sources or non-specific binding outside of the targeted region-of-interest. The extra sources of emitted light are noise signals and typically must be removed or excluded by post-processing methods in order to accurately quantify to the low-expressing protein.

Structured Illumination Microscopy (SIM) is an imaging technique, which involves the use of such post-processing methods in which an illumination pattern or mask, is used to allow spatial control of the illumination and resolution of the specific cell region of interest. This method is used for such applications as autofluorescence reduction, extended dynamic-range imaging, and optical depth sectioning.

However, a need exists for a method, which can be used during the image acquisition itself to target specific regions of interest or to locally increase contrast and signal to noise ratio. A real-time SIM process would improve efficiency or specificity of the fluorescent excitation and analysis of samples using prior information or specific features in a tissue image to adjust subsequent illumination patterns. To accomplish this however, the process requires that the acquired image and the illumination mask be registered such that the illumination mask can be precisely superimposed on the sample during subsequent image acquisition.

BRIEF DESCRIPTION

The present invention is directed to the imaging of protein expression and location in biological samples using optical segmentation.

According to one embodiment of the invention includes a method for optical segmentation of a biological sample positioned on a solid support and mounted on a fluorescent microscope. The method comprises transmitting light from a light source at a predetermined wavelength on to the biological sample wherein the light causes the biological sample to fluoresce; acquiring a fluorescent image of the biological sample using an image capture device; analyzing the fluorescent image utilizing, at least in part, featured based information or pixel intensity information to generate a masking pattern corresponding to a specific structure within the biological sample; transforming the masking pattern into a reformatted masking pattern to register the image of the image capture device with the spatial coordinates of a digital micro-mirror device (DMD); projecting the reformatted mask pattern onto the biological sample using the digital micro-mirror device (DMD) wherein said DMD is positioned between the light source and the biological sample and wherein the reformatted masked pattern is registered with the biological sample; acquiring a masked fluorescent image of the biological sample with the image capture device; and converting the masked fluorescent image into a digital image.

In another embodiment, the invention includes an image analysis system for optical segmentation of a biological sample positioned on a solid support. The image analysis system comprises a fluorescent microscope having a stage for mounting the biological sample; a light source for illuminating the biological sample and positioned such that light is directed through the aperature of the fluorecent microscope and onto the biological sample; a digital micro-mirror device (DMD) wherein said DMD is positioned between the light source and the aperature of the fluorecent microscope; an image capture device attached to the fluorescent microscope and configured to acquire fluorecent images of the biological sample; and a digital light processor. The digital light processor is configured to receive fluorescent images from the image capture device, analyzes the fluorescent image utilizing, at least in part, featured based information or pixel intensity information to generate a masking pattern wherein said masking pattern corresponds to a specific structure within the biological sample, and transform the masking pattern into a reformatted masking pattern to register the image of the image capture device with the spatial coordinates of the DMD.

DRAWINGS

These and other features, aspects, and advantages of the present invention will become better understood when the following detailed description is read with reference to the accompanying drawings in which like characters represent like parts throughout the drawings.

DETAILED DESCRIPTION

Figure 1:
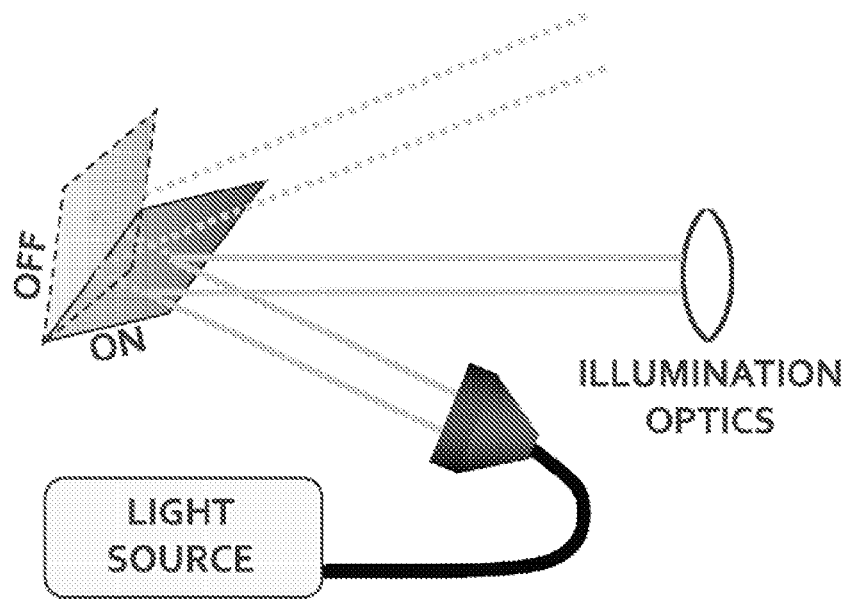
FIG. 1 is a schematic of a DMD operation showing light incident on the micro-mirror surface in an "ON" and "OFF" state.

In a conventional fluorescence imaging system, a spatially uniform light source is used to excite fluorescently labeled biomarkers of interest, resulting in the excitation of both exogenous fluorophores and endogenous fluorescent compounds found in a biological sample. If, however, a given protein is known to express primarily in a specific cell region such as the nuclei or epithelia, this information can be utilized to improve the efficiency or specificity of the fluorescent excitation. Excitation outside of the protein-expressing regions is avoided by first capturing a uniformly illuminated image of the structure of interest at a given channel, and using this image as the illumination mask for the channel corresponding to the marker of interest.

This invention relates generally to an image acquisition method that uses information obtained from a uniformly illuminated biological sample to selectively illuminate structural features of interest within the biological sample. The method involves creating a masking pattern, corresponding to a specific structure within the biological sample The specific structure is a high expressing morphological signal, including but not limited to membrane markers, vascular markers, nuclear stains, tumor markers, epithelial markers, or stromal markers.

The masking pattern created may be used in the illumination of regions where low-abundant markers are presumed to exist. Thus, the method is used to extend dynamic-range imaging of the sample by alleviating some of the issues associated with highly emitting sources within the sample, such as lipofuscin and red blood cells. For example, the dynamic range imaging for selected subcellular tissue regions may be optimized by sending more illumination where it is needed while avoiding the excitation of other objects within the sample such as red blood cells. In other words excitation of both exogenous fluorophores and endogenous fluorescent compounds found in a biological sample, which are not being targeted may be reduced. In addition, illumination masks designed using morphological markers may enable the detection of other biomarkers on specific cell and tissue structures.

In certain embodiments a biological sample may be mounted on a solid support and placed on a fluorescent microscope for analysis using a masking pattern, which is projected onto the biological sample. The term biological sample refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human). Furthermore a solid support refers to an article on which the biological sample may be immobilized and subsequently detected by the methods disclosed herein. The biological sample may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

Prior to imaging, the biological sample may be first labeled using molecular markers (dyes and antibodies) with fluorescent dyes or fluorophores. For example, cell nuclei can be stained with DAPI (a fluorescent dye that binds DNA specifically) while other regions in the tissue can be labeled immunofluorescently where the molecules of interest are targeted by directly conjugated antibodies, or by primary secondary amplification detection. For some structures, such as red blood cells (RBC) autofluorescence may occur.

The method to create the masking pattern comprises transmitting light from a light source at a predetermined wavelength on to the biological sample wherein the light causes the biological sample to fluoresce. In certain embodiments, the biological sample is illuminated uniformly across the surface. In other embodiments image information obtained from prior scans or similar samples may be used to selectively illuminate the sample. Selective illumination may increase the subsequently captured widefield fluorescent image signal to noise ratio, fidelity, specificity, or a combination thereof.

A widefield fluorescent image of the biological sample may be captured, using an image capture device and transferred to a digital light processor (DLP) for analysis. The image is analyzed utilizes, at least in part, featured based information or pixel intensity information to generate a masking pattern corresponding to a specific structure within the biological sample.

The masking pattern may be reformatted using the DLP to register the widefield fluorescent image with the spatial coordinates of a digital micro-mirror device (DMD), which is positioned between the light source and the illumination optics of the imaging system and which is used to project the reformatted masked image on to the mounted biological sample. Reformatting the image into the DMD coordinates removes variation in image resolution related to differences in array densities between the widefield image and the DMD devices, thus refining the placement of the superimposed image.

The DMD may be comprised of various pixel arrays. In certain embodiments the DMD may be a MEMS-mirror that allows light to be directed either into or away from the illumination path, or a liquid crystal devise. MEMS-mirrors (Micro-electro-mechanical Systems) are lithographically produced mirrors that are operated with voltage signals applied through integrated circuits produced with similar lithographic techniques. These mirrors typically have dimensions measured in millimeters or fractions of millimeters. In certain embodiments, the micro-mirrors comprising the DMD are positioned in one of two angles corresponding to the "ON" and "OFF" states. In order to switch between states, each mirror is individually rotated about its diagonal axis. The light reflected off of each micro-mirror is either directed into the illumination optics of the microscope in the "ON" state, or deflected away from the microscope entrance in the "OFF" state, as shown in FIG. 1.

Figure 2:
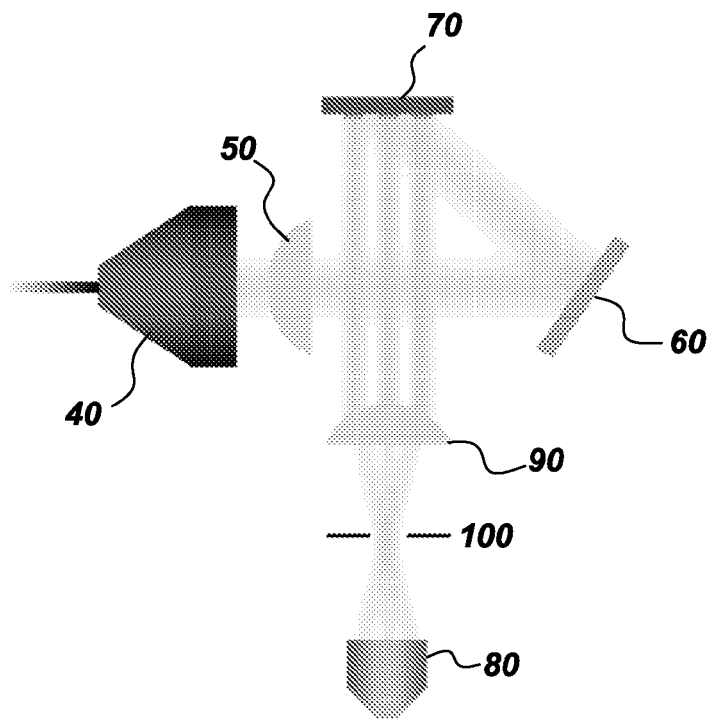
FIG. 2 is a schematic showing an illumination path through an illumination system using a DMD device for directing light.

FIG. 2 is an illustration of one embodiment of the invention showing an illumination path through a system, which would be attached to a microscope. A collimator lens 40 focuses a light from a light source (not shown) through an imaging element 50, such as but not limited to an aspheric lens, where it is reflected off a broadband mirror 60 to the DMD 70. Light incident on the DMD micro-mirror surface, which is directed into the microscope objective 80, passes through an asphere imaging lens 90 onto a field stop aperture 100.

By focusing the image onto the field stop in the illumination path shown in FIG. 2, the DMD pattern is sharply imaged onto the sample so long as the sample itself is in focus. The field stop is conjugate to the focal plane of the objective and as such, an image, which is coplanar with the field stop, will be relayed to the focal plane of the objective.

In order for an image acquired on the camera to be used as the DMD pattern, an affine transformation may be applied to match the scale, translation, and shift that occurs as the image is projected through the microscope optics. An affine transformation refers to any transformation that preserves collinearity such that all points lying on a line initially still lie on a line after transformation and ratios of distances, the midpoint of a line segment, remains the midpoint after transformation.

In addition to the need for an affine transformation, there may be a mismatch in the form factors. For example, the DMD may have a mirror array measuring 768×1024 mirrors whereas the camera sensor may have a pixel array measuring 1728×2352 pixels. Thus, the process of reformatting a camera image for use on the DMD may involve down sampling since the final format has fewer pixels than the original camera image.

Figure 3:
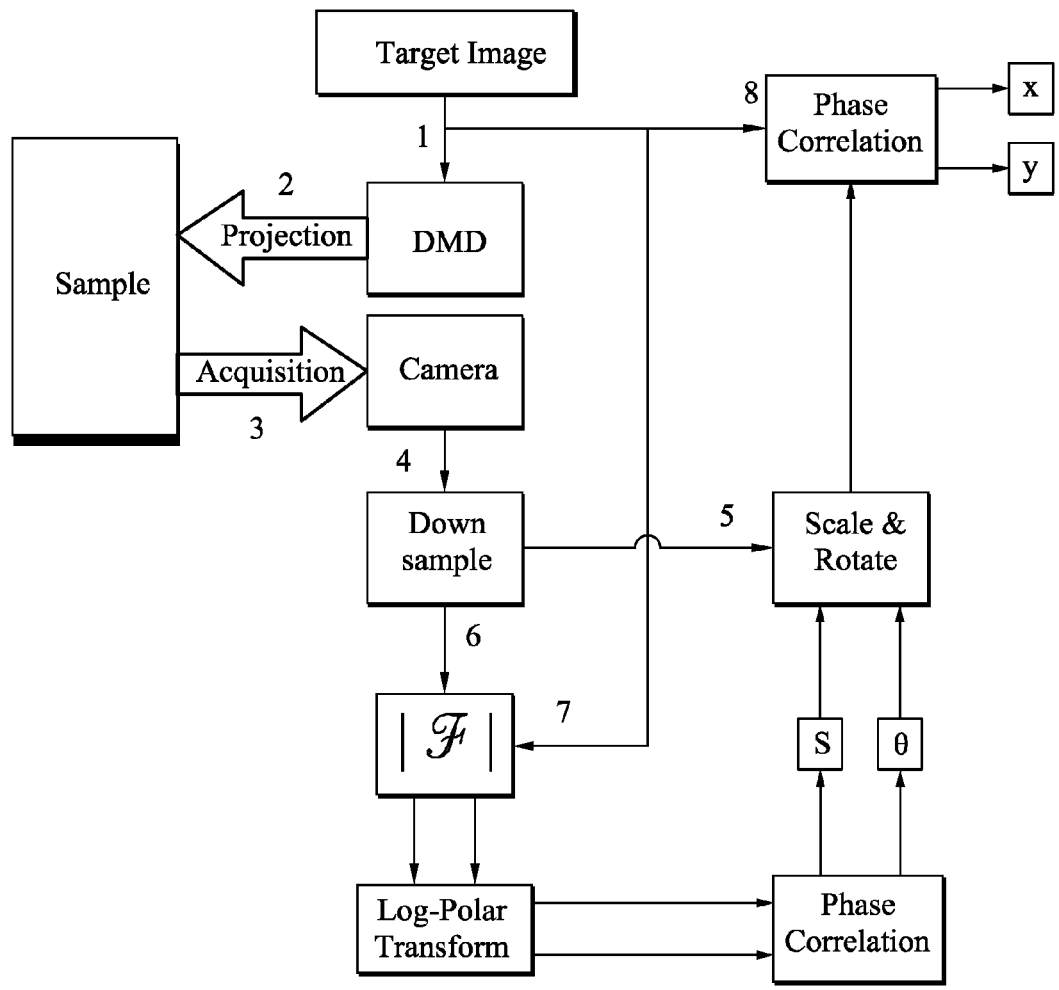
FIG. 3 is a flowchart showing one calibration routine that may be used to solve the parameters that map the camera coordinates to those of the DMD.

Once the transform parameters are known, these may be applied to an image acquired on the camera to yield a reformatted image that can be uploaded to the DMD. The reformatted image, when projected through the microscope, will be correctly registered with the sample. FIG. 3 is a flowchart showing one calibration routine that may be used to solve the affine parameters that map the camera coordinates to those of the DMD. The image of the target is registered to the original image to solve the parameters S, x, and y or scale, rotation, x shift, and y shift, respectively.

In one embodiment, as shown in FIG. 3, a target image is uploaded (1) onto the DMD and projected onto a calibration sample (2). The image of this target on the sample is acquired (3) with a microscope camera. The sample may then be down selected (4) to match form factors between the two images to create a resampled camera image. The resampled camera image and the target DMD image is registered and is used to solve for the affine transform parameters, rotation, scaling, and x-y translation between the two images (5 and 6). Once the transform parameters are calculated, the parameters may be stored, (7) applied to the registration of biological sample images using the same microscope camera and DMD (8).

Figure 4A:
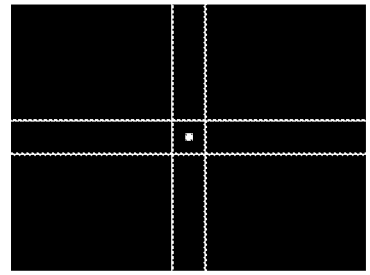
FIG. 4 is micrograph of a target DMD image used for calibrating camera images to match the DLP coordinates.
Figure 4B:
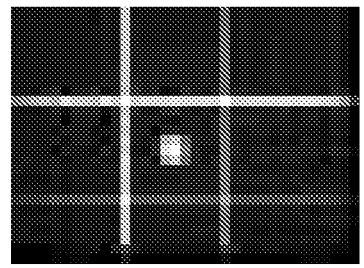
Figure 4C:
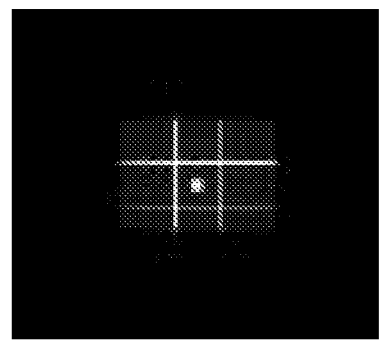

In one embodiment, a calibration routine may use a target DMD image for transform parameters whereby the DMD image uses well-defined features such as corners and straight lines to facilitate robust registration between the target and its projection on the sample plane. A calibration target image used for this type of calibration is shown in FIG. 4 and consists of a thin layer of highly concentrated Cy3 dye pressed between a glass slide and cover slip. This target resulted in a bright, uniform layer of fluorescence when observed with a Cy3 filter set. The thinness of the dye layer ensured a narrow range of best focus with high contrast. FIG. 4 shows, the DMD target image (A) along with its projections on the sample before (B) and after registration (C).

Given the target DMD projection on to the object has 768×1024 pixels and the image on the camera has 1728×2352 pixels, resampling the camera image may be used to produce matching form factors between the two images before registration. In certain embodiments, bilinear interpolation is used to determine pixel values at non-integer coordinates of the camera image.

In certain embodiments a 2D tapering or edge filtering function, such as a Hanning window may be used. For example, the image such as that shown in FIG. 4 may be multiplied by a 2D Hanning window function in order to smoothly taper the outer 50 pixels of the images down to zero. Such tapering windows may be used to avoid the presence of edge artifacts, which can be mistaken as image features in registration. After windowing, the target DMD image, and the resampled camera image may be registered to solve for the affine transform parameters.

Given the rotation, scaling, and x-y translation between the two images, appropriate transforms may be applied to systematically isolate and solve each of the parameters.

In certain embodiments, a Fourier Transform may be used as shifting an image does not change the magnitude of its Fourier Transform. Therefore, by considering only the magnitude of the Fourier Transform of each image, image registration may be limited to factors of rotation and scale. Rotation of an image results in an equal rotation of its Fourier Transform magnitude. Scaling an image by a factor of $\alpha$ yields a scaled Fourier Transform magnitude by a factor of $1/\alpha$. These parameters, however, are often difficult to measure directly from the Fourier Transform. An alternative approach may be to represent the Fourier Transform magnitude in log-polar space.

A log-polar transform may be applied, as it casts the image into radial and angular coordinates, which essentially converts scale and rotation into translation over the $\rho$ and $\theta$ axes. The magnitude of the Fourier Transform of the images are:

$$C = \log(abs(F(c)))$$

and $$D = \log(abs(F(d)))$$

where c and d represent the camera and DMD images, respectively, after multiplication by a Hanning window. Images C and D are shown in FIG. 5, wherein the upper row is the full image and the lower row shows a zoomed in area.

Figure 5:
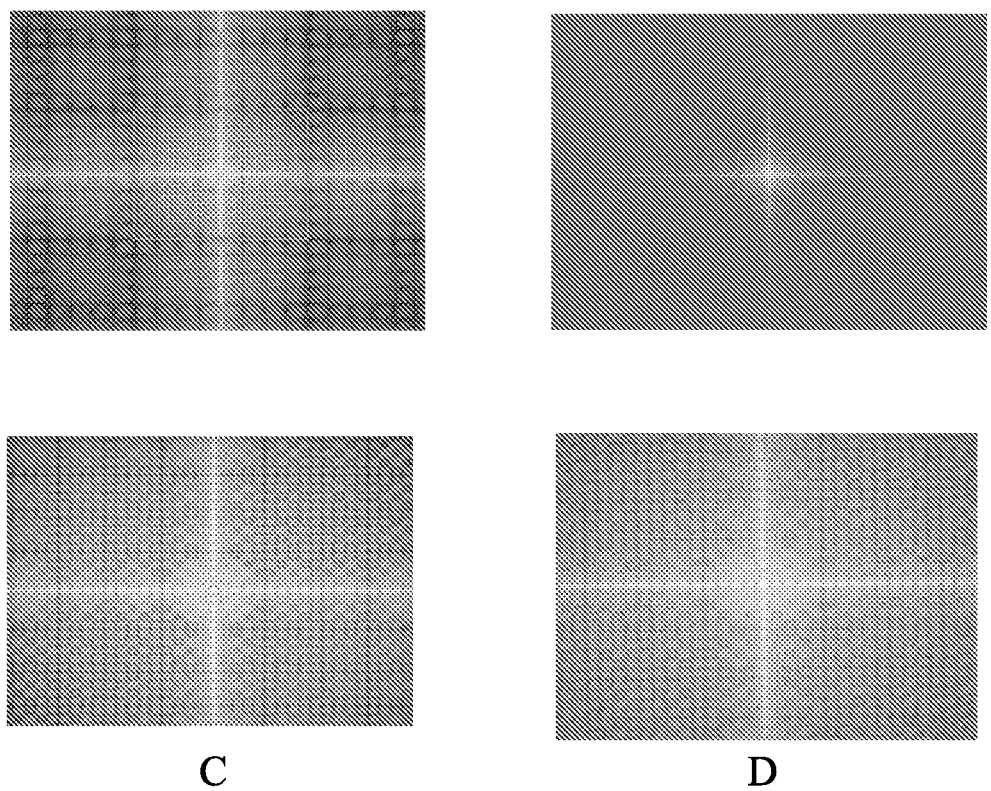
FIG. 5 are micrographs of the camera and DMD images, after multiplication by a Hanning window.

As observed in FIG. 5, image C is a scaled and rotated version of D, as such, the polar transforms, Cp and Dp, have the following relation:

$$Cp(\rho;\theta) = Dp(\rho/\alpha, \theta - \theta')$$

where $\alpha$ is the scaling factor, and $\theta'$ is the rotation in degrees. Rotation is thus reduced to translation along the $\theta$ axis. In order to reduce the scaling factor to a translation along the radial axis, the $\rho$ axis may be represented using a log scale. The result is the log polar images, $C_{lp}$ and $D_{lp}$, which have the relation $$C_{lp}(\rho;\theta) = D_{lp}(\log(\rho) - \log(\alpha), \theta - \theta')$$

The scaling factor may now be solved by finding the translation, log(a), in log-polar space, and exponentiating as follows:

$$a = e^{\log(a)}$$

Figure 6A:
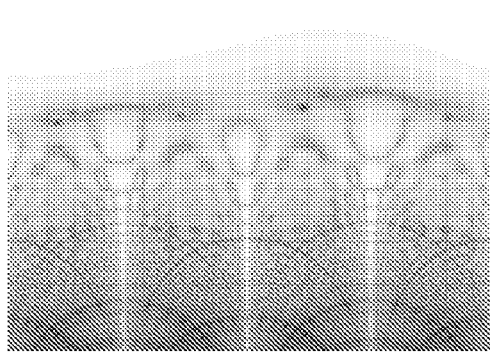
FIG. 6 are micrographs of a log-polar transform of the Fourier Transform magnitudes of DMD (A) and camera (B) images.
Figure 6B:
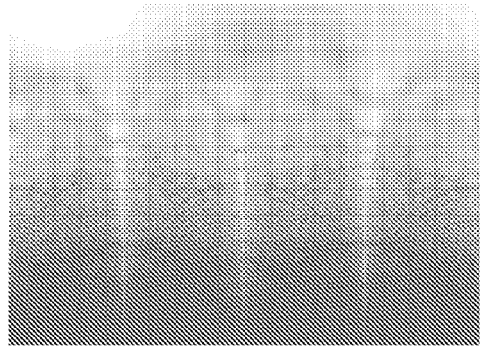

Likewise, the rotation is determined by solving for the shift along the $\rho$ axis. The log-polar representations, $C_{lp}$ and $D_{lp}$ are shown in FIG. 6. FIG. 6 are micrographs of the log-polar transform of the Fourier Transform magnitude of DMD (A) and camera (B) images. These transforms took the center, or DC term, of the Fourier transform as the center, and therefore convert the scale and rotation observed in the previous Fourier transform to translation along the $\rho$ and $\theta$ axes.

Translation may be determined using phase correlation, a frequency domain technique that determines the relative shift of two images based on their phase offset. The phase correlation from two images, a and b, may be determined by first computing the normalized cross power spectrum of the two signals, defined as:

$$R = AB^*/[AB^*]$$

where A and B are the Fourier Transform of the images, a and b. In this case, a and b are the log polar transforms, $C_{lp}$ and $D_{lp}$. The function r is then obtained from the inverse Fourier Transform of R. The lateral shifts correspond to the horizontal and vertical position of the peak of r:

$$(\Delta x; \Delta y) = \mathrm{argmax}(r).$$

This technique may be used to solve the log(r) and $\theta$ shifts in the log polar plot. Similarly, after applying the scale and rotation, the two resulting images differ only by a shift in x and y. Phase correlation may be applied to find the x and y translation on the two images.

EXPERIMENTAL

Structured illumination was implemented using the DLP® DISCOVERY™ 4000 (Texas Instruments Inc., Dallas Tex.) a commercially available DMD development board. This module enables 8-bit grayscale images to be uploaded and displayed at XGA resolution (768×1024 pixels). The EXFO X-CITE® 120Q (EXFO Electro-Optical Engineering Inc., Quebec, Canada), a broadband mercury lamp was used as the illumination source for the system. A liquid light guide is used to channel the output light from the lamp to a collimating lens. A 200 mm focal length asphere then focuses the collimated beam to a spot roughly the size of the DMD (0.7" diagonal length). The path of the focused beam is first directed at the appropriate angle with a turning mirror before focusing onto the face of the DMD. Finally, a 100 mm aspheric double of 2" diameter is used to relay the image of the DLP onto the field stop of an Olympus® BX-51 microscope (Olympus America Inc., Center Valley, Pa.).

A. Dynamic Range Extension

Figure 7:
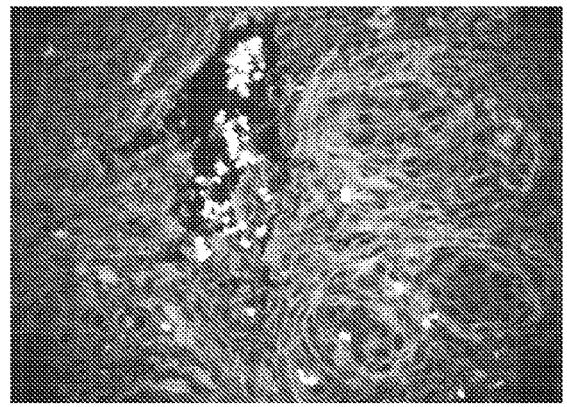
FIG. 7 is a micrograph of a uniformly illuminated prostate sample imaged at 300 ms exposure time, the time at which red blood cells cause saturation.
Figure 8:
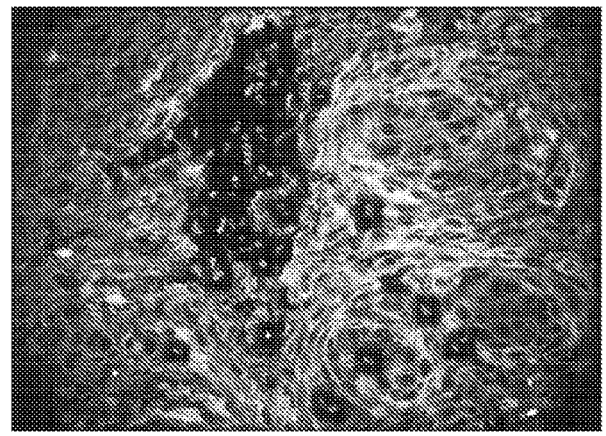
FIG. 8 is a micrograph of a prostate sample image at 900 ms exposure time using an illumination mask that reduces the excitation to previously saturate regions.

Varying the illumination intensity spatially may be used to reduce the amount of signal emitted from regions that would otherwise saturate the detector. This is demonstrated using a prostate sample containing red blood cells, which is imaged in the Cy3 channel as shown in FIG. 7. Red blood cells fluoresce with a great enough intensity to surpass the dynamic range of the camera, leaving the signal of interest at a relatively low signal to noise ration (SNR) as a result. After illuminating with a mask that reduced excitation to the red blood cells, the integration time was tripled without saturating the detector. This is shown in FIG. 8. Averaging over a 0.35 megapixel area of the signal region revealed an average pixel value of 43.1 in the saturated uniformly illuminated image, compared with an average value of 91.9 in the same region with structured illumination.

The use of structured illumination provided a greater than 2×increase in the average signal while avoiding saturation. This result demonstrates an effective increase in the dynamic range of the system to handle strong autofluorescent sources. In the case of saturation, illumination masks are formed by using a uniformly illuminated image and setting the saturated pixels to zero.

B. Optical Segmentation

Optical segmentation of biological structures is performed by acquiring an image of the sample stained for a morphological feature of interest. By processing this image, an illumination mask is created that allows excitation to reach only those regions that correspond the structures of interest. Using this mask in different channels enables the segmentation of any biomarker within the spatial bounds of the biological sample's morphological structures corresponding to the mask. This has been demonstrated in various tissue samples for the segmentation of epithelial vs. stromal nuclei.

Figure 9A:
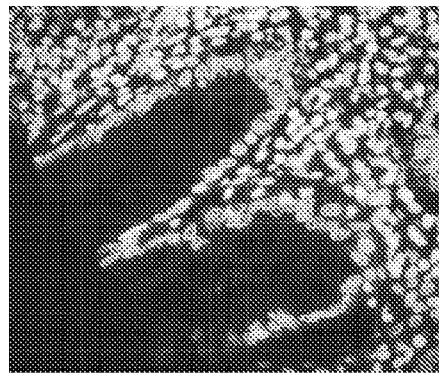
FIG. 9 is a micrograph of a colon sample imaged in the DAPI channel showing the stained nuclei (A), keratin staining in the Cy3 band (B) and epithelial nuclei (C) imaged in the DAPI channel using the keratin image as an illumination mask.
Figure 9B:
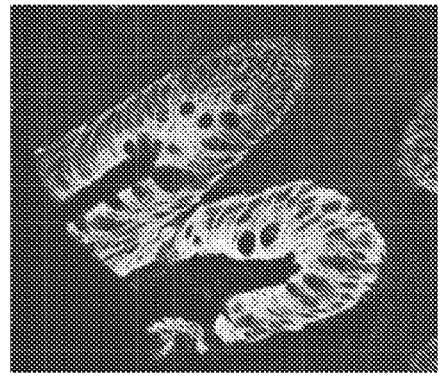
Figure 9C:
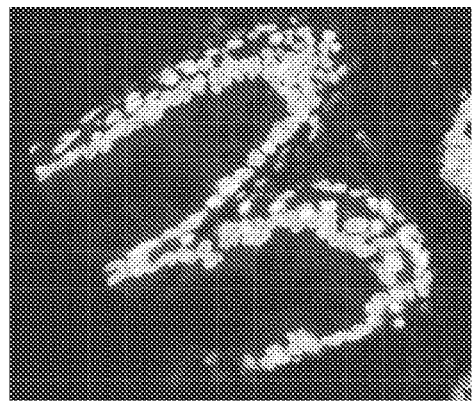

FIG. 9 is an example of colon tissue, which is stained for keratin and nuclei; stained nuclei imaged in the DAPI channel (A), keratin staining in the Cy3 band (B), and epithelial nuclei imaged in the DAPI channel using the keratin image as an illumination mask (C). Keratin, an abundant protein of the epithelium, is stained in the Cy3 band with the nuclei stained in DAPI. Given the CY3 channel image of the epithelium, a histogram normalization followed by thresholding gives a binary map of the epithelial tissue. This map is then registered and delivered to the DMD. Switching to the DAPI channel and applying the epithelial illumination mask will allow only the epithelial nuclei to be excited.

The invention includes embodiments that relate generally to using biological samples for analytical, diagnostic, or prognostic applications such as analyte detection, histochemistry, immunohistochemistry, or immunofluorescence. In some embodiments, the methods disclosed herein may be particularly applicable in histochemistry, immunostaining, immunohistochemistry, immunoassays, or immunofluorescence. In some embodiments, the methods disclosed herein may be particularly applicable in immunoblotting techniques, for example, western blots or immunoassays such as enzyme-linked immunosorbent assays (ELISA).

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method for optical segmentation of a biological sample positioned on a solid support and mounted on a fluorescent microscope comprising:
   transmitting light from a light source at a first predetermined wavelength on to the biological sample wherein the light causes the biological sample to fluoresce;
   acquiring a wide field fluorescent image of the biological sample using an image capture device;
   transferring the wide field fluorescent image to a digital light processor (DLP);
   analyzing the wide field fluorescent image utilizing, at least in part, feature based information or pixel intensity information;
   generating a masking pattern corresponding to a specific structure within the biological sample;
   transforming the masking pattern into a reformatted masking pattern, such that the said reformatted masking pattern comprises spatial coordinates of a digital micromirror device (DMD) and are registered to the wide field fluorescent image of the biological sample, wherein said DMD is positioned between the light source and the biological sample
   projecting the reformatted masking pattern onto the biological sample using the digital micro-mirror device (DMD);
   transmitting light from the light source at a second predetermined wavelength on to the biological sample through the reformatted mask pattern, wherein the light causes the biological sample to fluoresce;
   acquiring a masked fluorescent image of the biological sample with the image capture device; and
   converting the masked fluorescent image into a digital image.

2. The method of claim 1 wherein the transforming the masking pattern into a reformatted masking pattern comprises applying affine transformation parameters to the masking pattern.

3. The method of claim 2 wherein the affine transformation parameters are calculated using a calibration procedure wherein said calibration procedure comprises:
   uploading a target image onto the DMD and projecting said image onto a calibration sample;
   acquiring a calibration image of the target image projected onto the calibration sample;

down selecting the calibration image to match form factors between the image capture device with the spatial coordinates of a digital micro-mirror device (DMD) to create a reformatted image; and registering the reformatted image with the target image and solving for the affine transform parameters.

4. The method of claim 3 wherein the down selecting comprises applying a bilinear interpolation and 2D tapering function to images from the image capture device.

5. The method of claim 3 wherein solving for the affine transform parameters comprises applying a Fourier Transform operation to image registration.

6. The method of claim 5 wherein magnitude of the Fourier Transform operation is represented in log-polar space.

7. The method of claim 1 wherein projecting the reformatted mask pattern onto the biological sample results in varying the spatial illumination of the biological sample.

8. The method of claim 7 wherein varying the spatial illumination of the biological sample extends the dynamic range of image capture device by reducing the excitation of non-targeted exogenous fluorophores or endogenous fluorescent compounds found in the biological sample.

9. The method of claim 7 wherein varying the spatial illumination of the biological sample allows for optical segmentation of one or more biomarkers with the spatial bounds of the masked image.

10. The method of claim 1 wherein the converting the masked fluorescent image into a digital image represents a positive or negative image of the reformatted mask pattern.

11. The method of claim 1 wherein acquiring a fluorescent image of the biological sample comprises using image information from prior images to selectively illuminate the sample for increasing said fluorescent images signal to noise ratio, fidelity, specificity, or a combination thereof.

12. An image analysis system for optical segmentation of a biological sample positioned on a solid support comprising:
a fluorescent microscope having a stage for mounting the biological sample;
a light source configured to illuminate the biological sample at a first predetermined wavelength, and illuminate the biological sample at a second predetermined wavelength wherein the light of the second predetermined wavelength is directed through a reformatted masking pattern and wherein the light source is positioned such that light is directed through an aperture of the fluorescent microscope and onto the biological sample;
a digital micro-mirror device (DMD) wherein said DMD is positioned between the light source and the aperture of the fluorescent microscope;
an image capture device attached to the fluorescent microscope and configured to acquire fluorescent images of the biological sample; and
a digital light processor configured to:
receive wide field fluorescent images from the image capture device;
analyze the wide field fluorescent images utilizing, at least in part, feature based information or pixel intensity information;
generate a masking pattern corresponding to a specific structure within the biological sample; and
transform the masking pattern into the reformatted masking pattern, such that the said reformatted masking pattern comprises spatial coordinates of the DMD and are registered to the wide field fluorescent image of the biological sample, wherein said DMD is positioned between the light source and the biological sample to register the image of the image capture device with the spatial coordinates of the DMD.

13. The system of claim 12 wherein the digital light processor is configured to apply affine transformation parameters to the masking pattern.

14. The system of claim 13 wherein the digital light processor is further configured to store affine transformation parameters from one or more previously analyzed samples.

15. The system of claim 14 wherein the previously analyzed sample is from a calibration sample.

16. The system of claim 12 wherein the DMD is a two dimensional MEMS mirror array configured such that light incident on the individual micro-mirror surface is either deflected into or away from the aperture of the fluorescent microscope such that a pattern image can be projected onto the biological sample.

17. The system of claim 12 wherein the digital light processor is further configured to use image information from prior images to control the illumination of the biological sample and wherein the said illumination increases the acquired fluorescent image signal to noise ratio, fidelity, specificity, or combination thereof.

* * * * *

UNITED STATES PATENT AND TRADEMARK OFFICE
CERTIFICATE OF CORRECTION

PATENT NO.        : 8,532,398 B2
APPLICATION NO.   : 12/732272
DATED             : September 10, 2013
INVENTOR(S)       : Filkins et al.

It is certified that error appears in the above-identified patent and that said Letters Patent is hereby corrected as shown below:

In the Specification

In Column 2, Line 4, delete "aperature" and insert -- aperture --, therefor.

In Column 2, Line 7, delete "aperature" and insert -- aperture --, therefor.

In Column 2, Line 37, delete "is" and insert -- is a --, therefor.

In Column 3, Line 9, delete "sample" and insert -- sample. --, therefor.

In Column 6, Line 33, delete "relation" and insert -- relation: --, therefor.

In the Claims

In Column 8, Line 59, in Claim 2, delete "affme" and insert -- affine --, therefor.

In Column 8, Line 61, in Claim 3, delete "affme" and insert -- affine --, therefor.

In Column 9, Line 6, in Claim 3, delete "affme" and insert -- affine --, therefor.

In Column 9, Line 11, in Claim 5, delete "affme" and insert -- affine --, therefor.

In Column 10, Line 26, in Claim 13, delete "affme" and insert -- affine --, therefor.

In Column 10, Line 29, in Claim 14, delete "affme" and insert -- affine --, therefor.

Signed and Sealed this
Twenty-fifth Day of November, 2014

Michelle K. Lee
*Deputy Director of the United States Patent and Trademark Office*